US010179039B2

(12) United States Patent
Laurencin et al.

(10) Patent No.: US 10,179,039 B2
(45) Date of Patent: Jan. 15, 2019

(54) BI-PHASIC 3-DIMENISONAL NANOFIBER SCAFFOLDS, TWO PARALLEL BEAM COLLECTOR DEVICE AND METHODS OF USE

(71) Applicant: University of Connecticut, Farmington, CT (US)

(72) Inventors: Cato T. Laurencin, Avon, CT (US); Shaun W. McLaughlin, Farmington, CT (US); James Veronick, Durham, CT (US); Yusuf Kahn, Hamden, CT (US); Lakshmi S. Nair, Avon, CT (US); David J. Goldhamer, Storrs, CT (US)

(73) Assignee: University of Connecticut, Farmington, CT (US)

( * ) Notice: Subject to any disclaimer, the term of this patent is extended or adjusted under 35 U.S.C. 154(b) by 659 days.

(21) Appl. No.: 14/302,336

(22) Filed: Jun. 11, 2014

(65) Prior Publication Data

US 2014/0364948 A1 Dec. 11, 2014

Related U.S. Application Data

(60) Provisional application No. 61/833,577, filed on Jun. 11, 2013.

(51) Int. Cl.

| | |
|---|---|
| ***A61F 2/08*** | (2006.01) |
| ***A61L 27/50*** | (2006.01) |
| *A61F 2/00* | (2006.01) |

(52) U.S. Cl.
CPC ................ *A61F 2/08* (2013.01); *A61L 27/50* (2013.01); *A61F 2/0077* (2013.01); *A61F 2002/0894* (2013.01); *A61F 2240/001* (2013.01); *A61L 2400/12* (2013.01); *A61L 2430/30* (2013.01)

(58) Field of Classification Search
CPC combination set(s) only.
See application file for complete search history.

(56) References Cited

PUBLICATIONS

Jingwei Xie,Xiaoran Li, Justin Lipner, Cionne N. Manning, Annie G. Schwartz, Stavros Thomopoulos and Younan Xia; "Aligned-to-random" nanofiber scaffolds for mimicking the structure of the tendon-to-bone insertion site; Received Mar. 16, 2010, Accepted Mar. 29, 2010; Nanoscale; 2; 923-926.*

Li, W. J., C. T. Laurencin, E. J. Caterson, R. S. Tuan, and F. K. Ko. "Electrospun Nanofibrous Structure: A Novel Scaffold for Tissue Engineering." J Biomed Mater Res 60, No. 4 (2002): 613-21.

(Continued)

*Primary Examiner* — Yashita Sharma
(74) *Attorney, Agent, or Firm* — McDonnell Boehnen Hulbert & Berghoff LLP

(57) ABSTRACT

A biphasic scaffold and devices and methods for making the scaffold are disclosed. An example scaffold may include (a) a first plurality of randomly-oriented nanofibers defining a first tab region, (b) a second plurality of randomly-oriented nanofibers defining a second tab region, and (c) a plurality of aligned nanofibers coupled to and extending between the first tab region and the second tab region, where the plurality of aligned nanofibers are suspended between the first tab region and the second tab region.

8 Claims, 7 Drawing Sheets

(56) References Cited

PUBLICATIONS

Aviss, K. J., J. E. Gough, and S. Downes. "Aligned Electrospun Polymer Fibres for Skeletal Muscle Regeneration." Eur Cell Mater 19 (2010): 193-204.

Choi, J. S., S. J. Lee, G. J. Christ, A. Atala, and J. J. Yoo. "The Influence of Electrospun Aligned Poly(Epsilon-Caprolactone)/Collagen Nanofiber Meshes on the Formation of Self-Aligned Skeletal Muscle Myotubes." Biomaterials 29, No. 19 (2008): 2899-906.

Liang, D., B. S. Hsiao, and B. Chu. "Functional Electrospun Nanofibrous Scaffolds for Biomedical Applications." Adv Drug Deliv Rev 59, No. 14 (2007): 1392-412.

Pham, Q. P., U. Sharma, and A. G. Mikos. "Electrospinning of Polymeric Nanofibers for Tissue Engineering Applications: A Review." Tissue Eng 12, No. 5 (2006): 1197-211.

Wang, H. B., M. E. Mullins, J. M. Cregg, A. Hurtado, M. Oudega, M. T. Trombley, and R. J. Gilbert. "Creation of Highly Aligned Electrospun Poly-L-Lactic Acid Fibers for Nerve Regeneration Applications." J Neural Eng 6, No. 1 (2009): 016001.

Lee, W. Y., W. Y. Cheng, Y. C. Yeh, C. H. Lai, S. M. Hwang, C. W. Hsiao, C. W. Huang, M. C. Chen, and H. W. Sung. "Magnetically Directed Self-Assembly of Electrospun Superparamagnetic Fibrous Bundles to Form Three-Dimensional Tissues with a Highly Ordered Architecture." Tissue Eng Part C Methods 17, No. 6 (2011): 651-61.

Li, W. J., R. L. Mauck, J. A. Cooper, X. Yuan, and R. S. Tuan. "Engineering Controllable Anisotropy in Electrospun Biodegradable Nanofibrous Scaffolds for Musculoskeletal Tissue Engineering." J Biomech 40, No. 8 (2007): 1686-93.

* cited by examiner

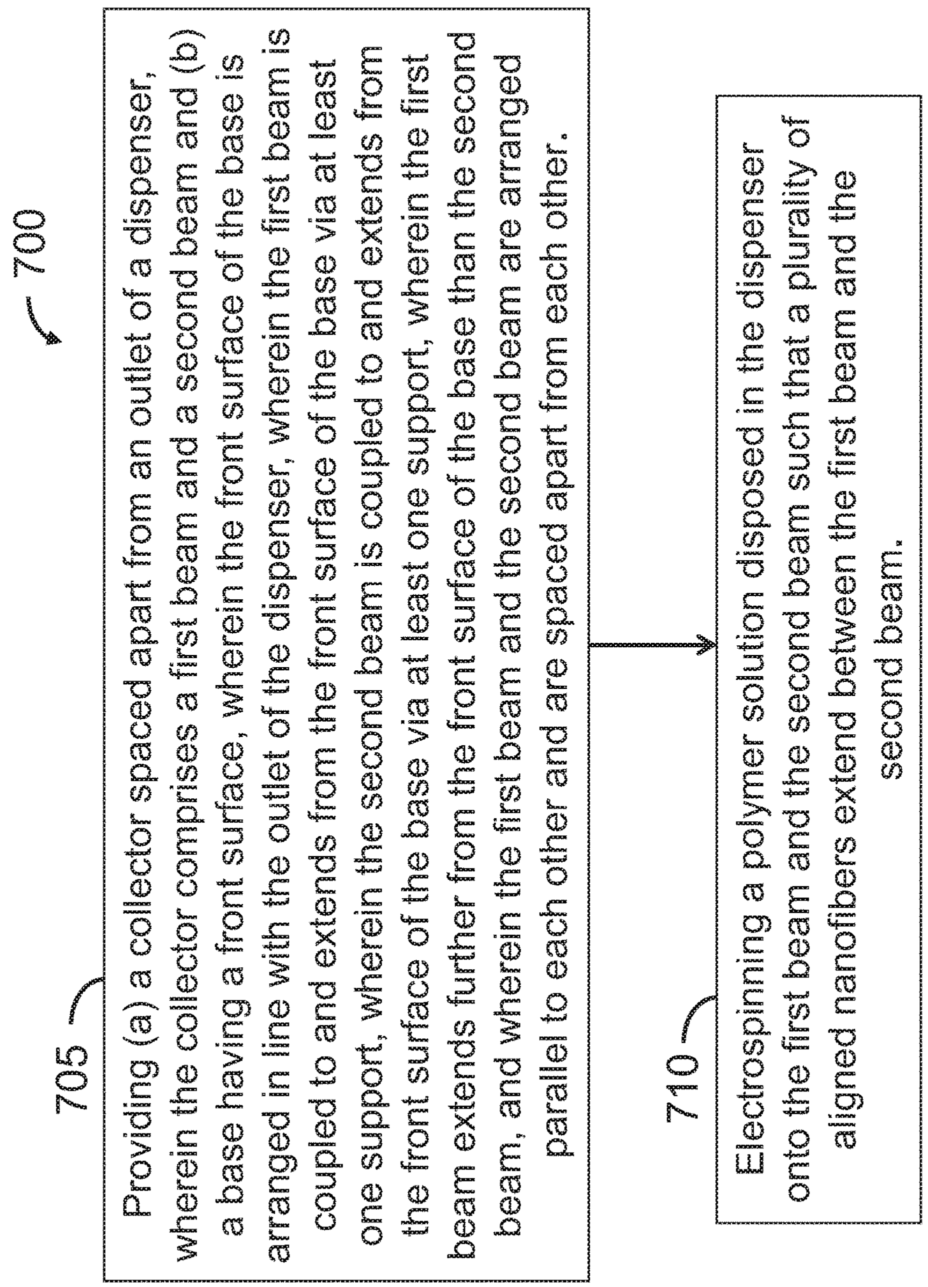

705 — Providing (a) a collector spaced apart from an outlet of a dispenser, wherein the collector comprises a first beam and a second beam and (b) a base having a front surface, wherein the front surface of the base is arranged in line with the outlet of the dispenser, wherein the first beam is coupled to and extends from the front surface of the base via at least one support, wherein the second beam is coupled to and extends from the front surface of the base via at least one support, wherein the first beam extends further from the front surface of the base than the second beam, and wherein the first beam and the second beam are arranged parallel to each other and are spaced apart from each other.

710 — Electrospinning a polymer solution disposed in the dispenser onto the first beam and the second beam such

BI-PHASIC 3-DIMENISONAL NANOFIBER SCAFFOLDS, TWO PARALLEL BEAM COLLECTOR DEVICE AND METHODS OF USE

CROSS-REFERENCE TO RELATED APPLICATION

This application claims the benefit of the filing date of U.S. Provisional Patent Application Ser. No. 61/833,577, filed Jun. 11, 2013, which is hereby incorporated by reference in its entirety.

BACKGROUND

Unless otherwise indicated herein, the materials described in this section are not prior art to the claims in this application and are not admitted to be prior art by inclusion in this section.

A population of stem cells, satellite stem cells ("SSCs"), naturally resides within adult skeletal muscle. These cells expand and differentiate in response to injury, maintaining the reparative and regenerative capacity of skeletal muscle. For example, one function of these cells is to repair minor damage to skeletal muscle from minor injuries and trauma. However, once an injury becomes too great, the satellite cells may fail to perform their function properly and scar tissue may develop. A limitation that leads to the failure of studies using SSCs for muscle regeneration is inadequate delivery and engraftment of the satellite cells into defective muscle tissue. Current approaches using nanofiber-based scaffolds as stem cell delivery vehicles suffer from various limitations, including unaligned fiber accumulation and/or collection of nanofibers directly onto a flat 2D surface, which limits application to in vivo systems.

SUMMARY

Example embodiments beneficially provide biphasic scaffolds, methods of treatment using the scaffolds and devices and methods for utilizing the device to make the scaffolds. These biphasic scaffolds have a plurality of aligned nanofibers extending between two tab regions each defined by a plurality of randomly-oriented nanofibers such that the aligned nanofibers are suspended and unsupported by a surface along their length. As such, the aligned nanofibers are not limited by geometric constraints on any surface. In addition, the tab regions of these scaffolds may advantageously exhibit structural properties of tendons and the aligned nanofibers may advantageously exhibit structural properties of muscle fibers to aid with cell seeding and/or in vivo implantation of the scaffold. For example, muscle uniquely requires cell alignment during regeneration in order to ensure proper anisotropic organization that facilitates functional contraction. Thus, the scaffold provided herein may be used to direct cells to undergo a phenomenon known as contact guidance. In various embodiments, the contact guidance may, for example, cause muscle satellite stem cells to differentiate into mature, multinucleated muscle fibers. Accordingly, muscle cells or their progenitors, such as satellite stem cells, seeded on aligned nanofiber surfaces may organize their actin along the direction of the fibers, and parallel F-actin may be critical for the formation of sarcomere, which is the contractile unit of the muscle fiber. As such, the scaffolds, devices and methods taught herein may further permit seeded cells to elongate along the aligned nanofibers in a manner similar to naturally occurring muscle regeneration. Moreover, since the suspended nature of the nanofibers imitates the individual mammalian muscle fiber structure, this may cause the cells to occupy similar locations on muscle fiber. Thus, the biphasic scaffold may recapitulate the native environment the cells reside in in vivo. So the scaffold may act as a delivery system for cells in vivo and may regenerate damaged areas of muscle previously thought beyond repair.

Thus, in one aspect, a scaffold is provided including the features of (a) a first plurality of randomly-oriented nanofibers defining a first tab region, (b) a second plurality of randomly-oriented nanofibers defining a second tab region, and (c) a plurality of aligned nanofibers directly coupled to and extending between the first tab region and the second tab region, wherein the plurality of aligned nanofibers are suspended between the first tab region and the second tab region.

In a second aspect, another scaffold is provided including the features of at least one nanofiber folded back and forth in a repeating manner such that the at least one nanofiber defines (a) a first tab region including a plurality of overlapping folds of the at least one nanofiber, (b) a second tab region including a plurality of overlapping folds of the at least one nanofiber and (c) a suspended region including aligned sections of the at least one nanofiber extending between the first tab region and the second tab region.

In a third aspect, a method for treating a muscle injury is provided including administering to a subject with a muscle injury the scaffold according to the first or second aspect at a site of the muscle injury in an amount effective to treat the muscle injury, wherein the scaffold is seeded with proteins, antibiotics, peptides, bioactive molecules, muscle cells, muscle progenitor cells, satellite stem cells, marrow-derived cells, mesenchymal stem cells, induced pluripotent cells or embryonic stem cells.

In a fourth aspect, a device for making a nanofiber scaffold is provided including the features of (a) a dispenser, (b) a power source coupled to an outlet of the dispenser, (c) a collector spaced apart from the outlet of the dispenser, wherein the collector comprises a first beam and a second beam, and (d) a base having a front surface, wherein the front surface of the base is arranged in line with the outlet of the dispenser, wherein the first beam is coupled to and extends from the front surface of the base via at least one support, wherein the second beam is coupled to and extends from the front surface of the base via at least one support, wherein the first beam extends further from the front surface of the base than the second beam extends, and wherein the first beam and the second beam are arranged parallel to each other and are spaced apart from each other.

In a fifth aspect, a method for making a nanofiber scaffold is provided including the steps of (a) providing (i) a collector spaced apart from an outlet of a dispenser, where the collector includes a first beam and a second beam and (ii) a base having a front surface, where the front surface of the base is arranged in line with the outlet of the dispenser, where the first beam is coupled to and extends from the front surface of the base via at least one support, where the second beam is coupled to and extends from the front surface of the base via at least one support, where the first beam extends further from the front surface of the base than the second beam, and where the first beam and the second beam are arranged parallel to each other and are spaced apart from each other and (b) electrospinning a polymer solution disposed in the dispenser onto the first beam and the second beam such that a plurality of aligned nanofibers extend between the first beam and the second beam.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 is a flow chart of a method for making a biphasic scaffold, according to one example embodiment.

DETAILED DESCRIPTION

Figure 1:
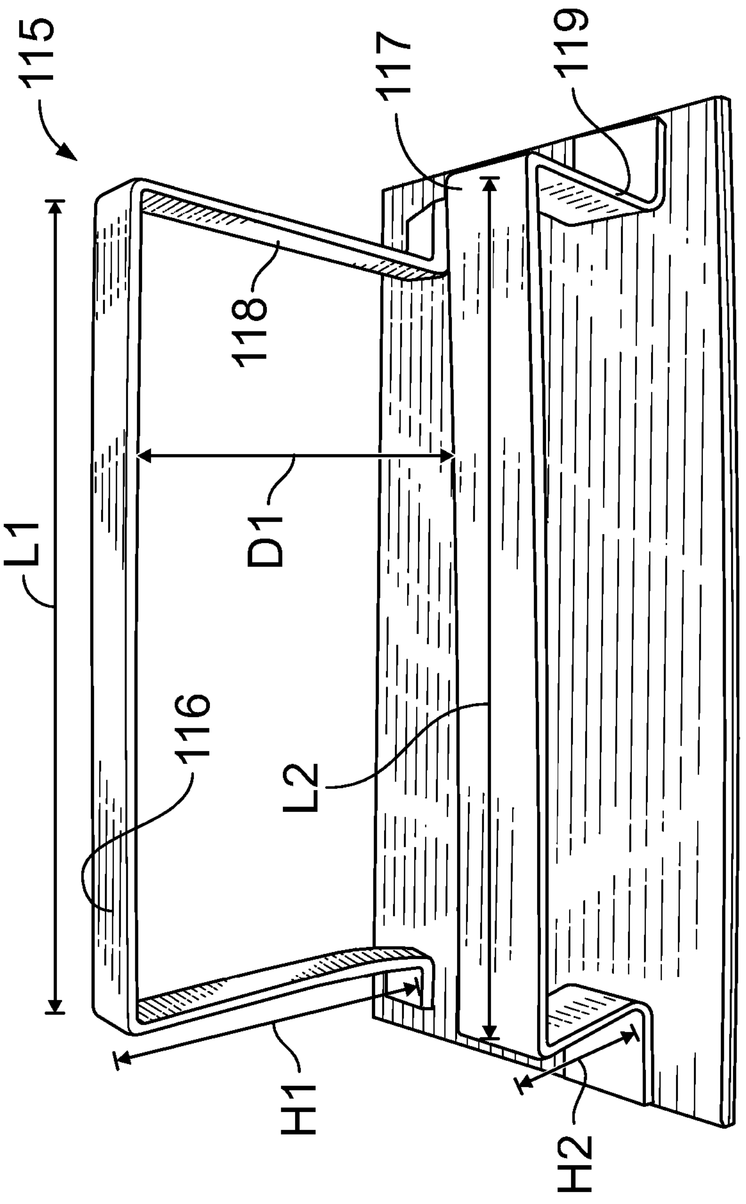
FIG. 1 is a photograph showing a top-front-facing perspective view of a spaced apart two-beam electrostatic collector, according to one example embodiment.

Example biphasic scaffolds, as well as methods of treatment using the scaffolds and devices and methods for making the biphasic scaffolds, are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "about" means+/−5%.

As used herein, "biphasic" means that a combination of aligned nanofibers and randomly-oriented nanofibers are present in discrete regions of the scaffold.

As used herein, "aligned" with respect to nanofibers means substantially, but not completely, arranged in a parallel manner.

As used herein, "randomly-oriented" with respect to nanofibers means arranged in a non-aligned manner such as in a mesh, criss-cross pattern, overlapping loops, fiber mat or intertwined manner, among other possibilities.

The aligned and randomly-oriented nanofibers may be derived from a continuous or discontinuous polymer solution stream. These nanofibers may comprise any suitable polymer, for example a biocompatible polymer. Exemplary polymers for use in the scaffolds of the present invention may include, but are not limited to polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. Suitable biodegradable polymers can be determined by those in the art in light of the disclosure herein and the intended purpose of the scaffold.

As used herein, "cells" means any cell type that may be used with the scaffold, including but not limited to any type of muscle cells or their progenitor cells, including but not limited to satellite stem cells, marrow-derived cells, mesenchymal stem cells, induced pluripotent cells, or embryonic stem cells. Also, the cells can be derived from any organism, including but not limited to mammals such as humans, dogs, cats, farm animals, etc.

As used herein, "suspended," with respect to nanofibers, means that the aligned nanofibers are not limited by geometric constraints on any surface and are unsupported by a surface along their length.

The present embodiments advantageously provide biphasic scaffolds, as well as methods of treatment using the scaffolds and devices and methods for making the biphasic scaffold. In one aspect, the invention provides a scaffold, comprising:

a first plurality of randomly-oriented nanofibers defining a first tab region, a second plurality of randomly-oriented nanofibers defining a second tab region, and a plurality of aligned nanofibers directly coupled to and extending between the first tab region and the second tab region, wherein the plurality of aligned nanofibers are suspended between the first tab region and the second tab region.

Figure 3:
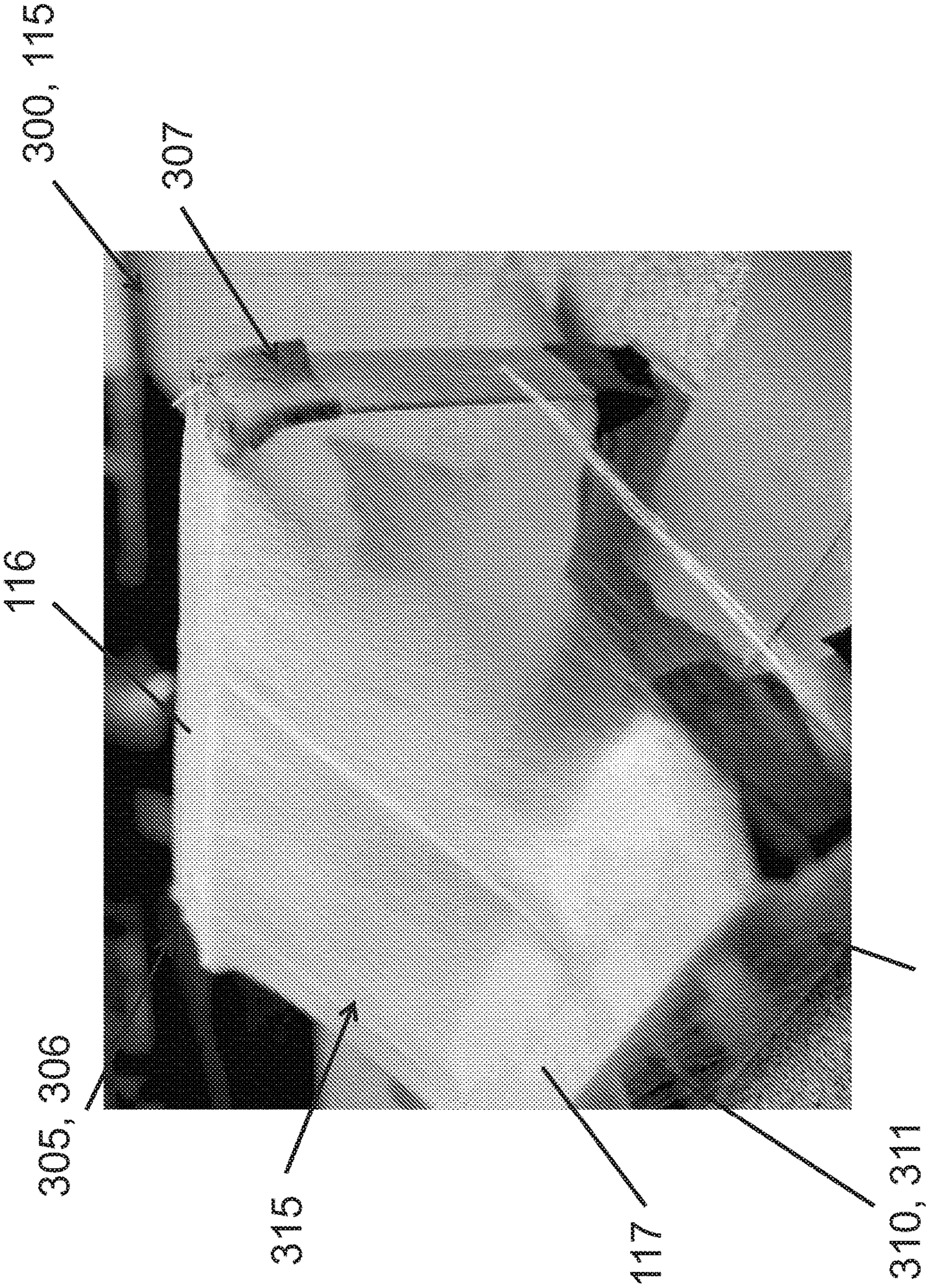
FIG. 3 is a photograph showing a perspective view of a scaffold of nanofibers electrospun onto the spaced apart two-beam collector of FIG. 1 using the schematic setup shown in FIG. 2. In this example embodiment, the scaffold was generated via 2 hours of electrospinning a 85:15 poly-lactic-co-glycolic acid ("PLGA") solution.
Figure 4B:
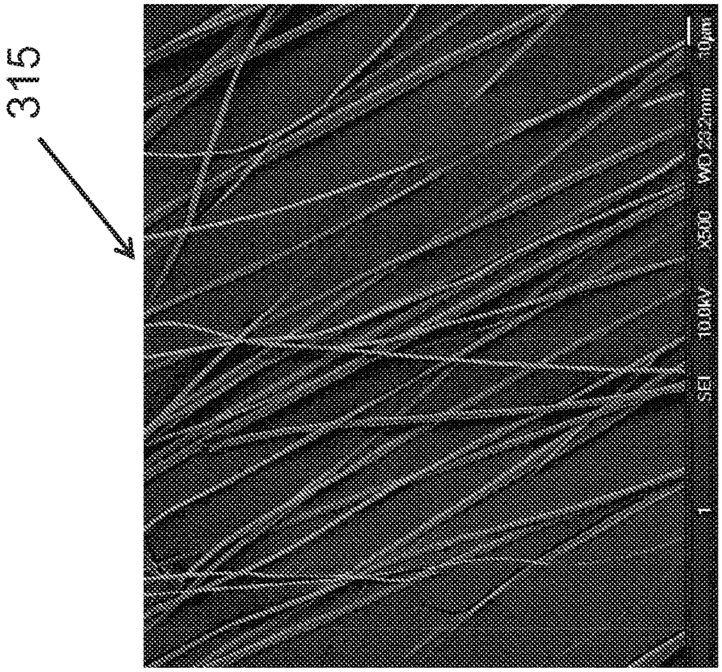
FIG. 4B shows a scanning electron microscope ("SEM") image of the plurality of aligned nanofibers showing their parallel organization and size distribution.
Figure 4A:
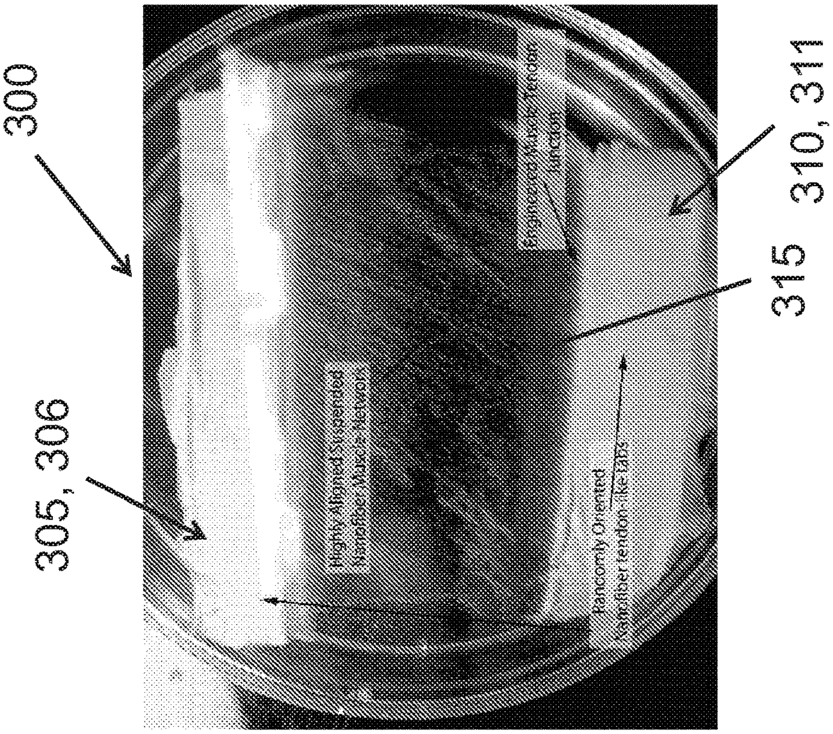
FIG. 4A shows the scaffold of FIG. 3 removed from the spaced apart two-beam collector, where a plurality of aligned nanofibers span the gap between two tab regions each defined by a plurality of randomly-oriented tendon-like nanofibers.

Referring now to FIGS. 3-4, a biphasic scaffold 300 is shown including a first plurality of randomly-oriented nanofibers 306 defining a first tab region 305. The scaffold 300 also includes a second plurality of randomly-oriented nanofibers 311 defining a second tab region 310. In another embodiment, the first and the second plurality of randomly-oriented nanofibers 306, 311 may comprise a mesh or overlapping loops, as shown in FIG. 4A. In another embodiment, the first and the second plurality of randomly-oriented nanofibers 306, 311 may have a thickness ranging from about 0.5 mm to about 10 mm. In practice, the tabs 305, 310 may replicate physiological organization of the muscletendon junction and the tab regions 305, 310 may aid in anchoring the scaffold for in vivo placement. For example, the randomly-oriented fibers 306, 311 defining the tab regions 305, 310 may provide a base for suturing that may have a greater tear strength than the region composed of the aligned nanofibers 315 described below.

The scaffold 300 further includes a plurality of aligned nanofibers 315 directly coupled to and extending between the first tab region 305 and the second tab region 310. In one embodiment, the plurality of aligned nanofibers 315 may be substantially parallel to each other, as shown in FIG. 4B. In a further embodiment, the plurality of aligned nanofibers 315 may have a diameter ranging from about 700 nm to about 1.5 μm. In one embodiment, the first plurality of randomly-oriented nanofibers 306 may define a first support 307 and the second plurality of randomly-oriented nanofibers 311 may define a second support 312 such that the plurality of aligned nanofibers 315 are suspended between the first and second supports 307, 312. The first and second supports 307, 312 may be removed or folded into the first and second tab regions 305, 310 prior to seeding with cells, prior to loading with bioactive molecules or prior to in vivo implantation. In various embodiments, the plurality of aligned nanofibers 315 may be suspended in air or in culture medium, for example, prior to in vivo implantation. In practice, the plurality of aligned nanofibers 315 may mimic mammalian like muscle fibers to aid in cell seeding or loading of biological materials.

In one embodiment, the support 307 of the first tab region 305 may be arranged substantially parallel to the support 312 of the second tab region 310. In a further embodiment, the support 307 of the first tab region 305 may have a height H1 at least 2 mm greater than a height H2 of the support 312 of the second tab region 310 and are each arranged at an angle relative to the plurality of aligned nanofibers 315 such that the plurality of aligned nanofibers 315 angle downward from the first tab region 305 to the second tab region 310.

Figure 5B:
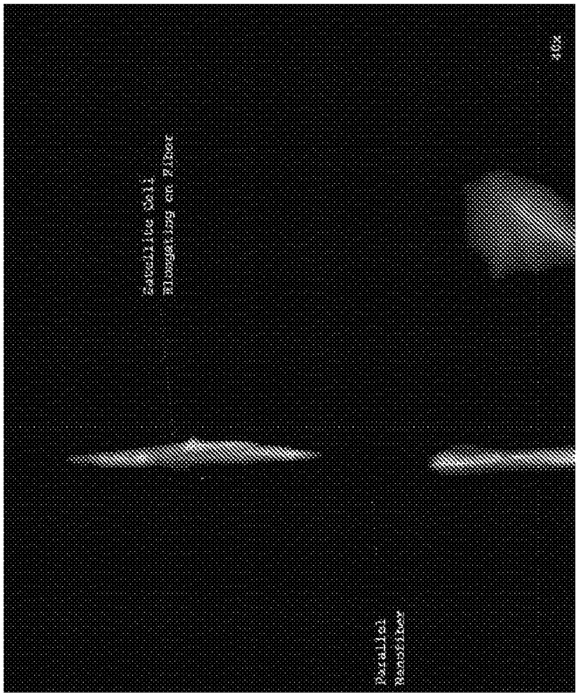
FIG. 5B shows an image of 48 hour actin staining of human satellite stem cells seeded on a scaffold, according to an example embodiment, illustrating a satellite cell elongated in the direction of a suspended aligned nanofiber.
Figure 5A:
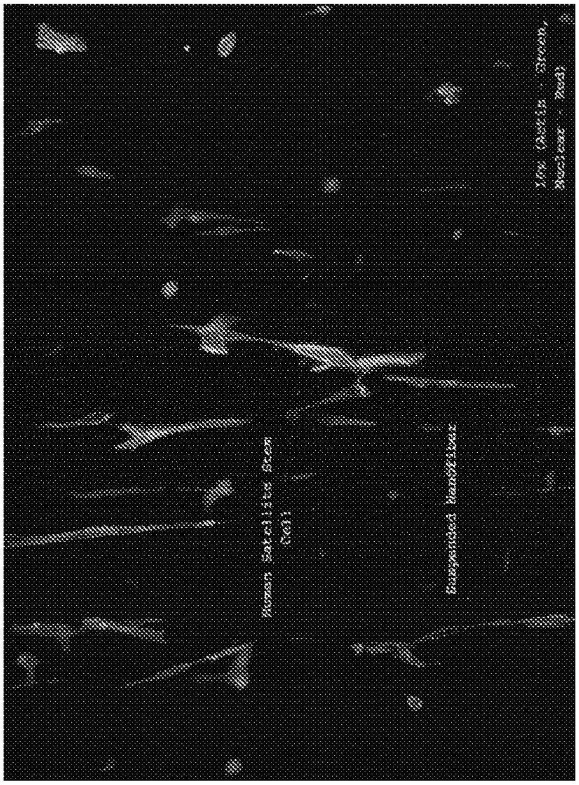
FIG. 5A shows an image of 48 hour actin staining of human satellite stem cells seeded on a scaffold, according to an example embodiment, illustrating that the arrangement of the plurality of aligned nanofibers suspended between two tab regions of randomly-oriented nanofibers permits cells to wrap around the individual fibers.
Figure 6B:
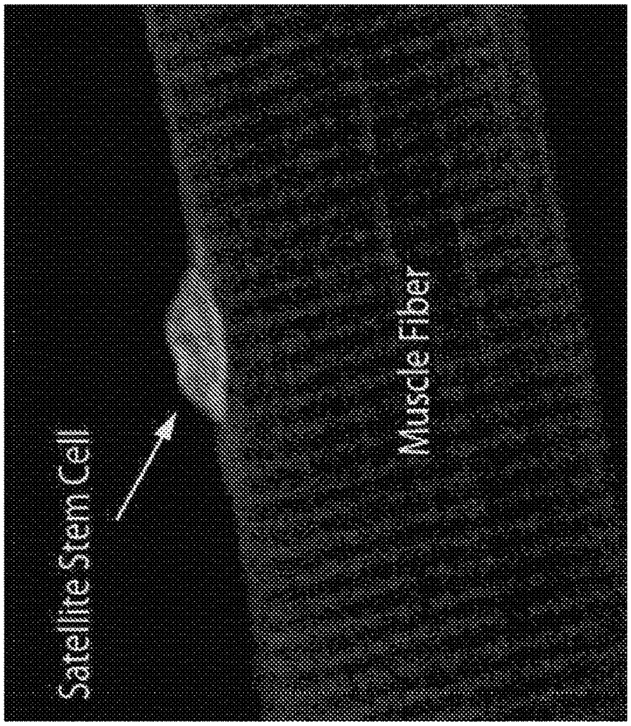
FIG. 6B shows an image of a satellite stem cell residing on a freshly isolated muscle fiber from a transgenic mouse model expressing a green fluorescent protein ("GFP").
Figure 6A:
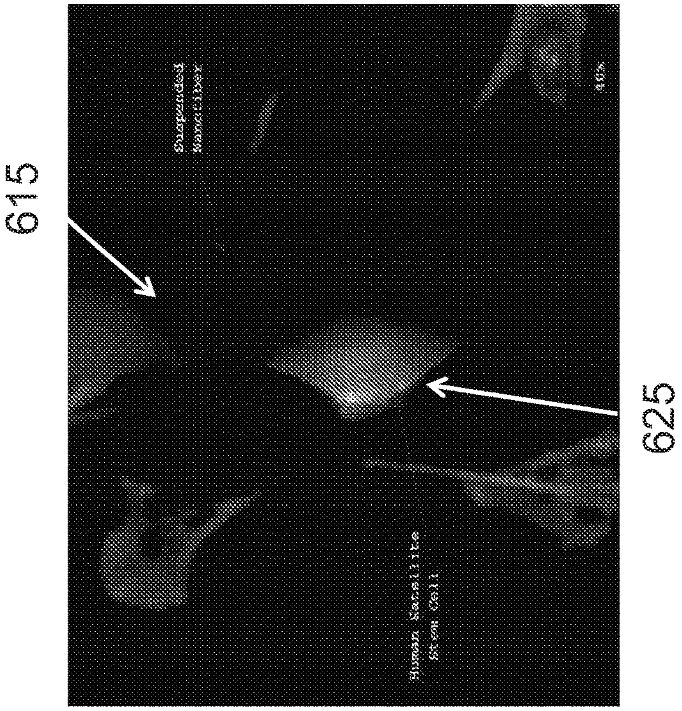
FIG. 6A shows an image of actin staining of a satellite stem cell growing on a suspended aligned nanofiber of a scaffold, according to an example embodiment.

In a further embodiment, a plurality of cells may be seeded on the plurality of aligned nanofibers 315 and on the plurality of randomly-oriented nanofibers 306, 311 of the first and the second tab regions 305, 310. In yet another embodiment, the plurality of cells may include any cell type that may be used with the scaffold, including but not limited to any type of muscle cells or their progenitor cells, including but not limited to satellite stem cells, myoblasts, marrow-derived cells, mesenchymal stem cells, induced pluripotent cells, or embryonic stem cells, among other possibilities. Also, the cells can be derived from any organism, including but not limited to mammals such as humans, dogs, cats, farm animals, etc. In operation, satellite stem cells may be seeded on the aligned nanofiber surfaces and may organize their actin along the direction of the nanofibers, as shown in FIGS. 5A, 5B. Since the suspended nature of the nanofibers may imitate the individual mammalian muscle fiber structure, this may cause cells to occupy similar naturally occurring locations on muscle fiber. As an example, contrast the seeded cell 620 on the nanofiber 615 in FIG. 6A with the naturally occurring satellite stem cell disposed on a muscle fiber in FIG. 6B.

In another aspect, the invention provides a scaffold comprising:

at least one nanofiber folded back and forth in a repeating manner such that the at least one nanofiber defines (a) a first tab region comprising a plurality of overlapping folds of the at least one nanofiber, (b) a second tab region comprising a plurality of overlapping folds of the at least one nanofiber and (c) a suspended region comprising aligned sections of the at least one nanofiber extending between the first tab region and the second tab region.

In one embodiment, the at least one nanofiber may be formed from a continuous stream of polymer solution that is arranged in a back and forth manner via whipping instability induced through electrospinning. In the regions where the polymer stream reverses direction, the polymer stream folds over on itself forming a mesh or overlapping loops, for example. In addition, the polymer stream extends from one fold to the next fold and is suspended between the folds.

In another aspect, the invention provides a method for treating a muscle injury, comprising:

administering to a subject with a muscle injury the scaffold according to the first or second aspect and/or various embodiments thereof at a site of the muscle injury in an amount effective to treat the muscle injury, wherein the scaffold is seeded with proteins, antibiotics, peptides, bioactive molecules, muscle cells, muscle progenitor cells, satellite stem cells, myoblasts, marrow-derived cells, mesenchymal stem cells, induced pluripotent cells or embryonic stem cells.

As used herein, a “muscle injury” means muscle tissue that has been negatively impacted by trauma, surgery or disease in a manner that interrupts the natural repair mechanisms of the body, induces excessive scar tissue formation, and/or significantly hinders muscle function. “Muscle injury,” as used herein, may also include serious loss in muscle mass as a result of trauma, surgery or disease, for example, loss in muscle mass in the amount of about 5% to about 20% or more.

As used herein, an “effective amount” means a scaffold sized to fit the injury site.

As used herein, “treating” the muscle injury comprises implanting a scaffold according to the first or second aspect in vivo adjacent to and in direct contact with the muscle injury.

As used herein, a “subject” includes any organism, including but not limited to mammals such as humans, dogs, cats, farm animals, etc.

In another aspect, the invention provides a device, comprising:

a dispenser, a power source coupled to an outlet of the dispenser, a collector spaced apart from the outlet of the dispenser, wherein the collector comprises a first beam and a second beam, and a base having a front surface, wherein the front surface of the base is arranged in line with the outlet of the dispenser, wherein the first beam is coupled to and extends from the front surface of the base via at least one support, wherein the second beam is coupled to and extends from the front surface of the base via at least one support, wherein the first beam extends further from the front surface of the base than the second beam extends, and wherein the first beam and the second beam are arranged parallel to each other and are spaced apart from each other.

Figure 2:
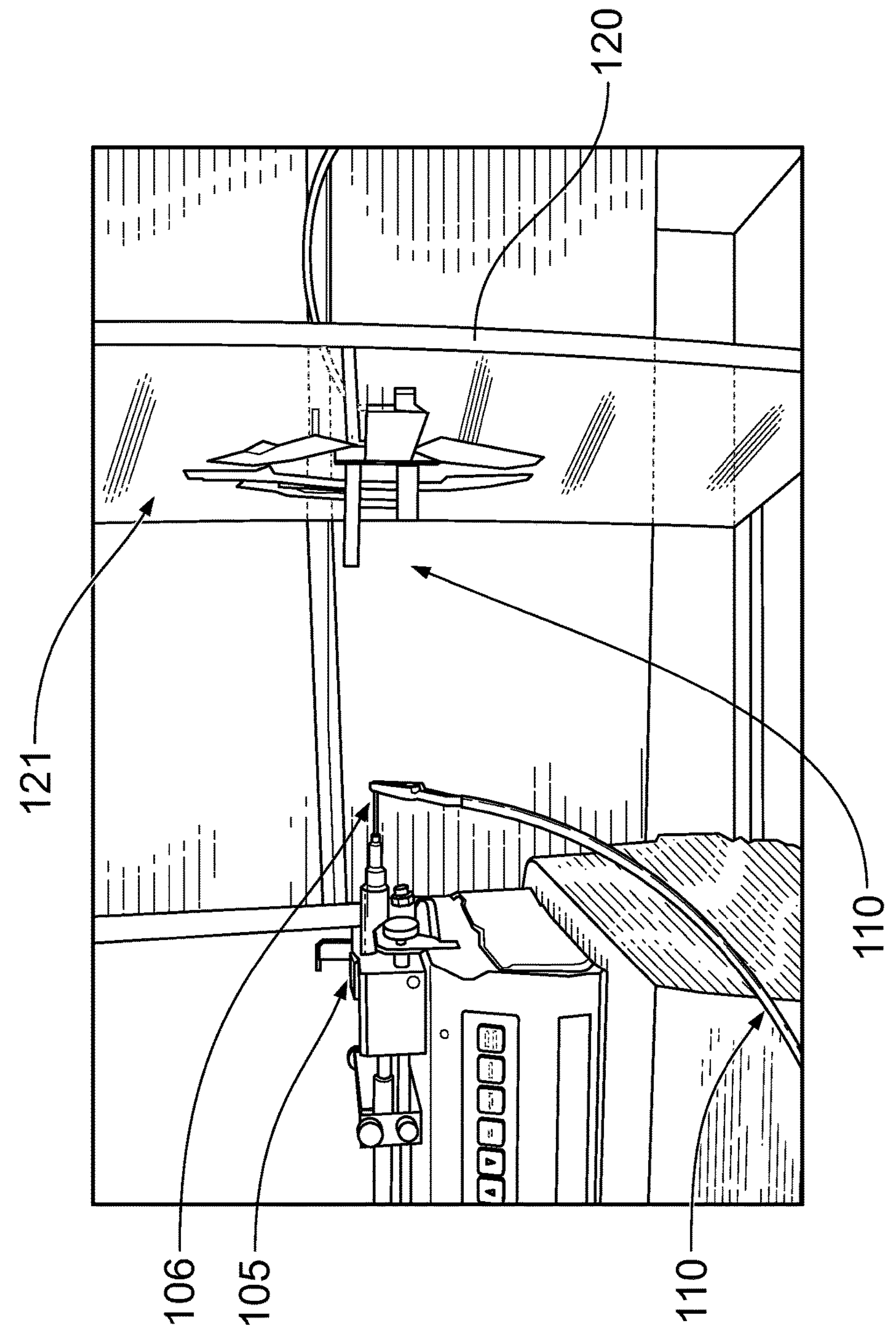
FIG. 2 is a photograph showing a side view of a schematic of the electrospinning system of the invention utilizing the spaced apart two-beam electrostatic collector of FIG. 1.

Referring now to FIGS. 1-3, a device 100 is shown including a dispenser 105 that is configured to hold a polymer solution. A power source 110 may be coupled to an outlet 106 of the dispenser 105 to induce electrospinning.

The device 100 also includes a collector 115 that is provided in the path of and spaced apart from the outlet 106 of the dispenser 105. In one embodiment, the collector 115 may be spaced apart from the outlet 106 of the dispenser 105 a distance ranging from about 1 cm to about 100 cm. In one embodiment, the collector 115 may be grounded to aid in electrospinning a polymer solution onto the collector.

Further, the collector 115 includes a first beam 116 and a second beam 117. The first beam 116 and the second beam 117 are arranged parallel to each other and are spaced apart from each other. The first and second beams 305, 310 may be spaced apart both in a vertical direction and/or a horizontal direction relative to the base 120 described below. The practical effect of this spaced arrangement is that a polymer stream directed out of the outlet 106 of the dispenser 105 is forced to lay across the first beam 116 and then across the second beam 117 and back again to the first beam 116 in a repeating fashion causing the fibers suspended therebetween to align. If the first beam 116 and the second beam 117 had the same height, then the fibers would not be forced to drape from one beam to the other. In various embodiments, the spacing of the first beam and the second beam in the horizontal and vertical directions may be customized to match a target in vivo application. For example, the collector may be adjusted to create scaffolds that custom fit a patient's injured muscle target zone by adjusting the horizontal distance D1 or the height H1, H2 of the first beam or second beam.

In another embodiment, the first beam 116 may have a higher electrostatic potential than the second beam 117. In various embodiments, the first beam 116 and the second beam 117 are electrically conductive and may comprise metal, such as stainless steel or aluminum, among other possibilities.

The device 100 further includes a base 120 that has a front surface 121. The front surface 121 of the base 120 is arranged in line with the outlet 106 of the dispenser 105. The base 120 may be made of either a conductive or a non-conductive material. The first beam 116 of the collector 115 is coupled to and extends from the front surface 121 of the base 120 via at least one support 118. The second beam 117 is likewise coupled to and extends from the front surface 121 of the base 120 via at least one support 119. The first beam 116 extends further from the front surface 121 of the base 120 than the second beam 117 extends. In one embodiment, the first beam 116 may extend from the front surface 121 of the base 120 a distance H1, and the second beam 117 may extend from the front surface 121 of the base 120 a distance H2. In another embodiment, the first beam 116 may be spaced apart from the second beam 117 a horizontal distance D1 relative to the base. In various embodiments, this distance D1 may be adjusted to match the size of a target muscle injury site. In a yet another embodiment, the first beam may extend from the front surface of the base at least 2 mm further than the second beam.

In a further aspect, the invention provides a method, comprising:

providing (a) a collector spaced apart from an outlet of a dispenser, wherein the collector comprises a first beam and a second beam and (b) a base having a front surface, wherein the front surface of the base is arranged in line with the outlet of the dispenser, wherein the first beam is coupled to and extends from the front surface of the base via at least one support, wherein the second beam is coupled to and extends from the front surface of the base via at least one support, wherein the first beam extends further from the front surface of the base than the second beam, and wherein the first beam and the second beam are arranged parallel to each other and are spaced apart from each other; and electrospinning a polymer solution disposed in the dispenser onto the first beam and the second beam such that a plurality of aligned nanofibers extend between the first beam and the second beam.

FIG. 7 is a flow chart of a method 700 for making a biphasic scaffold, according to one example embodiment. Example methods, such as method 100 of FIG. 1, may be carried out by an operator or a control system. A control system may take the form of program instructions stored on a non-transitory computer readable medium and a processor that executes the instructions. However, a control system may take other forms including software, hardware, and/or firmware.

As shown by block 705, method 700 involves providing (a) a collector spaced apart from an outlet of a dispenser, where the collector comprises a first beam and a second beam and (b) a base having a front surface, where the front surface of the base is arranged in line with the outlet of the dispenser, where the first beam is coupled to and extends from the front surface of the base via at least one support, where the second beam is coupled to and extends from the front surface of the base via at least one support, where the first beam extends further from the front surface of the base than the second beam, and where the first beam and the second beam are arranged parallel to each other and are spaced apart from each other. Then, at block 710, a polymer solution disposed in the dispenser is electrospun onto the first beam and the second beam such that a plurality of aligned nanofibers extend between the first beam and the second beam. A process called whipping instability may cause the nanofibers generated from a stream of the polymer solution to hit the first beam, which may have a higher electrostatic potential than the second beam, then the nanofibers may wrap around the second beam and the stream then continues back and forth between beams.

In addition, in one embodiment, electrospinning the polymer solution onto the first beam and the second beam may include depositing a stream of polymer solution back and forth between the first beam and the second beam. This forms a first plurality of randomly-oriented nanofibers at the first beam and a second plurality of randomly-oriented nanofibers at the second beam. In this arrangement, the plurality of aligned nanofibers directly couple the first plurality and the second plurality of randomly-oriented nanofibers to each other.

In another embodiment, electrospinning the polymer solution onto the first beam and the second beam may include applying a voltage to an outlet of the dispenser and expelling the polymer solution from the outlet of the dispenser.

In one embodiment, the thickness of the tab regions 305, 310 and the density of the suspended region 315 of the scaffold 300 may be increased by increasing the time period for electrospinning the polymer solution. As the thickness of the tab regions 305, 310 increases, the electrical conductivity of the collector 115 may not be as effective. Accordingly, in still another embodiment, method 700 may further include the step of severing the plurality of aligned nanofibers from first and second plurality of randomly-oriented nanofibers. Next, the polymer solution is electrospun onto the first and second plurality of randomly-oriented nanofibers on the collector. This forms a second plurality of aligned nanofibers extending between the first beam and the second beam and may result in thicker tab regions 305, 310.

The above detailed description describes various features and functions of the disclosed biphasic scaffolds, devices and methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A scaffold formed using a collector having a base and a first beam and a second beam horizontally spaced apart from each other, the first beam having a height greater than a height of the second beam relative to the base, the scaffold comprising:

a first plurality of randomly-oriented nanofibers defining a first tab region;

a second plurality of randomly-oriented nanofibers defining a second tab region; and a plurality of aligned nanofibers directly coupled to and extending between the first tab region and the second tab region, wherein the plurality of aligned nanofibers are suspended between the first tab region and the second tab region, wherein the first plurality of randomly oriented nanofibers further define a first support and the second plurality of randomly oriented nanofibers further define a second support such that the plurality of aligned nanofibers are suspended between the first support and the second support, wherein a height of the first support is greater than a height of the second support relative to the base of the collector and the first support and the second support are arranged parallel to each other and are each arranged at an angle relative to the plurality of aligned nanofibers such that the plurality of aligned nanofibers angle downward from the first tab region to the second tab region.

2. The scaffold of claim 1, wherein the plurality of aligned nanofibers are substantially parallel to each other and wherein the first and the second plurality of randomly-oriented nanofibers comprise a mesh, mat or overlapping loops.

3. The scaffold of claim 1, wherein the first and the second plurality of randomly-oriented nanofibers have a thickness ranging from about 0.5 mm to about 10 mm.

4. The scaffold of claim 1, wherein a plurality of cells or a plurality of biological materials are seeded on the plurality of aligned nanofibers and on the plurality of randomly-oriented nanofibers of the first and the second tab regions.

5. The scaffold of claim 4, wherein the plurality of cells comprise muscle cells, muscle progenitor cells, satellite stem cells, myoblasts, marrow-derived cells, mesenchymal stem cells, induced pluripotent cells or embryonic stem cells.

6. The scaffold of claim 4, wherein the plurality of biological materials comprise proteins, antibiotics, peptides, or bioactive molecules.

7. The scaffold of claim 1, wherein the plurality of aligned nanofibers have a diameter ranging from about 700 nm to about 1.5 μm.

8. A method for treating a muscle injury, comprising:

administering to a subject with a muscle injury a scaffold at a site of the muscle injury in an amount effective to treat the muscle injury, wherein the scaffold is seeded with proteins, antibiotics, peptides, bioactive molecules, muscle cells, muscle progenitor cells, satellite stem cells, myoblasts, marrow-derived cells, mesenchymal stem cells, induced pluripotent cells or embryonic stem cells, wherein the scaffold comprises (i) a first plurality of randomly-oriented nanofibers defining a first tab region, (ii) a second plurality of randomly-oriented nanofibers defining a second tab region; and (iii) a plurality of aligned nanofibers directly coupled to and extending between the first tab region and the second tab region, wherein the plurality of aligned nanofibers are suspended between the first tab region and the second tab region, wherein the first plurality of randomly oriented nanofibers further define a first support and the second plurality of randomly oriented nanofibers further define a second support such that the plurality of aligned nanofibers are suspended between the first support and the second support, wherein a height of the first support is greater than a height of the second support relative to the base of the collector and the first support and the second support are arranged parallel to each other and are each arranged at an angle relative to the plurality of aligned nanofibers such that the plurality of aligned nanofibers angle downward from the first tab region to the second tab region.

* * * * *